United States Patent [19]

Eilers et al.

[11] Patent Number: 5,602,002
[45] Date of Patent: Feb. 11, 1997

[54] PROCESS FOR THE PRODUCTION OF LOW-CHROMIUM PROTEIN HYDROLYZATES

[75] Inventors: Eberhard Eilers, Ulm; Andreas Sander, Illertissen, both of Germany

[73] Assignee: Gruenau Illertissen GmbH, Illertissen, Germany

[21] Appl. No.: 436,348

[22] PCT Filed: Nov. 10, 1993

[86] PCT No.: PCT/EP93/03151

§ 371 Date: Jul. 19, 1995

§ 102(e) Date: Jul. 19, 1995

[87] PCT Pub. No.: WO94/10856

PCT Pub. Date: May 26, 1994

[30] Foreign Application Priority Data

Nov. 19, 1992 [DE] Germany ............... 42 38 979.8

[51] Int. Cl.$^6$ .................................................. C12P 21/06
[52] U.S. Cl. ............... 435/68.1; 8/94.27; 435/265; 530/343; 530/356
[58] Field of Search ............... 435/68.1, 265; 530/356, 343; 8/94.27

[56] References Cited

U.S. PATENT DOCUMENTS

| | | | |
|---|---|---|---|
| 4,100,154 | 7/1978 | Holloway | 260/123.7 |
| 5,094,946 | 3/1992 | Taylor et al. | 435/68.1 |
| 5,271,912 | 12/1993 | Taylor et al. | 435/68.1 |

FOREIGN PATENT DOCUMENTS

| | | |
|---|---|---|
| 0972090 | 11/1952 | Germany . |
| 1000388 | 10/1953 | Germany . |
| 2252281 | 5/1973 | Germany . |
| 0212983 | 8/1984 | Germany . |
| 0287274 | 2/1991 | Germany . |
| 0055796 | 6/1991 | Hungary . |
| 1041717 | 9/1966 | United Kingdom . |

OTHER PUBLICATIONS

J. Am. Leather Chem. Assoc. 1990, 85, 264.
Cf. Das Leder 1991, 42, 133–143.
J. Am. Leather Chem. Soc. 1990, 85, 262.
"Bio Times" [quarterly magazine of the Novo Nordisk Company] 1990, 5, No. 1, pp. 4–5.
Jens Adler–Nissen, "Enyzmatic Hydrolysis of Food Proteins", Elsevier, London 1986.
Hollemann–Wiberg, "Lehrbuch der anorganischen Chemie", 81–90th Edition, p. 876.

Primary Examiner—Herbert J. Lilling
Attorney, Agent, or Firm—Wayne C. Jaeschke; John E. Drach; Henry E. Millson, Jr.

[57] ABSTRACT

Described is the chemical hydrolysis of partial hydrolysates obtained by the enzymatic decomposition, in aqueous conditions in the presence of alkaline-earth oxides or hydroxides, of protein-containing raw materials containing chromium. This enables protein hydrolysates with a particularly low chromium content to be obtained which are stable to turbidity during storage. The chemical hydrolysis must be carried out in the presence of compounds selected from the alkaline-earth oxides and hydroxides, and within the critical pH range of 11 to 13.

18 Claims, No Drawings

PROCESS FOR THE PRODUCTION OF LOW-CHROMIUM PROTEIN HYDROLYZATES

BACKGROUND OF THE INVENTION

1. Field of the Invention

This invention relates to a process for the production of low-chromium protein hydrolyzates.

2. Statement of Related Art

The fate of chromium shavings, which accumulate as waste products in the production of chrome-tanned leather, is a growing problem in the leather industry. The reason for this is that the presence of the chromium waste in dumps involves the risk of contamination of the ground water by Cr(III) and—after possible oxidation—even by Cr(VI). According to data provided by Taylor et al., 54,000 tonnes of chromium shavings accumulate annually in the USA alone (J. Am. Leather Chem. Assoc. 1990, 85, 264).

Boiling with alkali, usually lime or magnesium oxide, is one of the oldest methods for detanning chrome leather waste, cf. for example U.S. Pat. No. 4,100,154. According to the teaching of this patent, the alkaline hydrolysis of chrome leather is carried out at temperatures above about 90° C. in the presence of calcium oxide or calcium hydroxide. By increasing the reaction temperature, which can be achieved for example by carrying out the reaction in a pressure reactor, the hydrolytic degradation rate can be further increased. According to this document, chromium is removed to residues "below 5 ppm", although the exact concentrations of collagen hydrolyzate in the solutions and hence the reference value for the Cr content are not disclosed.

DE-A-1 000 388 describes a process for the production of protein degradation products in which the hydrolysis of chrome leather is carried out with water or aqueous ammonia at elevated temperature and pressure.

The desire to avoid the drastic reaction conditions of the conventional protein hydrolysis processes mentioned above has resulted in the development of enzymatic hydrolysis processes. For example, German patent application DE 22 52 281 describes a process for the hydrolysis of skin fragments using neutral or alkaline proteases which are capable of decomposing collagen. Leather fragments inter alia may be used as the skin fragments. Before the enzymatic treatment, the protein of the skin fragment is denatured by heating with water. The enzymatic hydrolysis is subsequently carried out at moderate temperatures of 20° to 70° C. and is typically followed by thermal denaturing of the enzyme and by filtration of the crude product obtained.

In a more recent publication, Heideman et al. discuss in detail possible methods for treating chromium shavings. So far as the hydrolysis of chromium shavings with proteases is concerned, they come to the conclusion that the preliminary denaturing of the shavings plays a critical role. They obtained optimal results when they first digested chromium shavings with 10% of lime for about 20 minutes and then treated the shavings with protease (cf. Das Leder 1991, 42, 133–143).

It has only recently been shown by Taylor et al. that preliminary denaturing is not absolutely essential in the enzymatic hydrolysis of chrome leather waste. In their method, the protein present in the waste is treated with special mixtures of alkali metal and alkaline earth metal compounds and alkalases at moderate temperatures without preliminary denaturing. The authors reported on their method at the 85th Annual Conference of the ALCA (J. Am. Leather Chem. Soc. 1990, 85, 262). In addition, this method is the subject of U.S. Pat. No. 5,094,946. Furthermore, the effectiveness of the method was confirmed in practical tests carried out at the Danish tannery Svendborg Fingarveri ("Bio Times" [quarterly magazine of the Novo Nordisk Company] 1990, 5, No. 1, pages 4–5). However, the method developed by Taylor et al. has the disadvantage that the aqueous concentrates thus prepared are not stable in storage, but instead become cloudy over a period of time.

DESCRIPTION OF THE INVENTION

Accordingly, the problem addressed by the present invention was to provide a process for the production of low-chromium protein hydrolyzates which would lead to clear, non-clouding products. Another problem addressed by the present invention was to provide a process for the production of protein hydrolyzates with a lower chromium content by comparison with the relevant prior art which is important in particular for the use of these products in cosmetics and in the food industry.

According to the invention, the solution to this problem is characterized in that chromium-containing protein-containing raw materials are first partly hydrolyzed in aqueous medium in the presence of an additive from the group of alkaline earth metal oxides or hydroxides and in the presence of proteolytic enzymes and the partial hydrolyzates obtained are subjected to chemical hydrolysis in the presence of alkaline earth metal oxides or hydroxides at a pH value in the range from 11 to 13.

Accordingly, the present invention relates to a process for the production of low-chromium protein hydrolyzates by hydrolysis of chromium-containing protein-containing raw materials, in which the chromium-containing protein-containing raw materials are first partly hydrolyzed in aqueous medium in the presence of an additive from the group of alkaline earth metal oxides or hydroxides and in the presence of proteolytic enzymes and the partial hydrolyzates obtained are then subjected to chemical hydrolysis—optionally after separation from the insoluble chromium salts formed by methods known per se—in the presence of alkali metal compounds from the group of alkaline earth metal oxides or hydroxides at a pH value of 11 to 13.

The process according to the invention has the advantage that, even in the form of concentrates with an active substance content of more than 40% by weight, the products obtained are stable against clouding in storage and, in addition, are distinguished by an extremely low chromium content.

The first step of the process according to the invention is carried out in known manner.

In a preferred embodiment of the present invention, the first step, i.e. the partial hydrolysis in the presence of proteolytic enzymes, is carried out without preliminary denaturing of the chromium-containing protein-containing raw material. This preferred embodiment essentially comprises a) initially introducing the raw material in aqueous medium,
b) introducing an alkaline earth metal oxide or hydroxide as additive to establish the required pH value and to provide a co-factor for the enzyme,
c) carrying out the reaction in the presence of a proteolytic enzyme at a temperature and a pH value which correspond to the optimum temperature and optimum pH of the protease used, typically at temperatures of 60° to 75° C. and at pH values of 10 to 11.

Reference is specifically made in this regard to U.S. Pat. No. 5,094,946. It may be desirable subsequently to separate the crude product obtained in the enzymatic hydrolysis into a partial hydrolyzate and a chromium-containing residue by a separation process such as sedimentation, centrifugation or filtration.

It has been found that, in the interests of process economy, "pH stattechnique" is particularly suitable for establishing the pH value in the first process step. In pH-stat technique, the fall in the pH value brought about by protons released during the enzymatic hydrolysis is counteracted by the continuous introduction of bases so that the pH is kept at a constant level (cf., for example, Jens Adler-Nissen, "Enyzymatic Hydrolysis of Food Proteins", Elsevier, London 1986). Where the pH-stat technique in question is applied, it is advisable to carry out the process in the vicinity of the pH-dependent optimum effect of the particular enzyme used.

The second step of the process according to the invention, i.e. the chemical hydrolysis, must be carried out in the presence of compounds from the group of alkaline earth metal oxides or hydroxides at a pH value of 11 to 13. Lower pH values only promote incomplete hydrolysis so that, on the one hand, the stability of the protein hydrolyzates to clouding and, on the other hand, the low chromium contents required for the aqueous protein hydrolyzate are not guaranteed. At higher pH values, the amphoteric chromium(III) hydroxide is in danger of redissolving (cf. Hollemann-Wiberg, "Lehrbuch der anorganischen Chemie", 81–90th Edition, page 876).

Basically, any chromium-containing protein-containing substances may be used as raw materials in the process according to the invention. However, the chrome leather waste accumulating during leather production in the tanneries is preferably used. By virtue of their particle size in the mm range, chromium shavings are particularly preferred. Accordingly, chrome leather waste of large surface area, for example leather rags, are best mechanically size-reduced before application of the process according to the invention.

The chemical hydrolysis which follows the enzymatic hydrolysis is preferably carried out at temperatures of 80° to 100° C. and more preferably at temperatures of 90° to 95° C. The duration of the chemical hydrolysis should be no less than 5 minutes, the upper limit being 60 minutes. Calcium hydroxide or calcium oxide is preferably used as the base during the chemical hydrolysis.

The chemical hydrolysis step does not require any special technological measures. Accordingly, it may be carried out in any mixer-equipped reactors. A tanning mixer is mentioned as an example of a suitable open reactor.

The crude product obtained after the chemical hydrolysis step is worked up in known manner. Working up generally comprises a) one or more filtration steps largely intended to remove the chromium hydroxide formed. For viscosity reasons, filtration is generally carried out at temperatures of 60° to 100° C. and, more particularly, at temperatures of 90° to 95° C.;

b) the precipitation of calcium ions, for example by addition of oxalic acid, and subsequent separation of the calcium oxalate formed, for example by filtration, or by addition of sodium carbonate and separation of the calcium carbonate precipitated;

c) concentration of the protein hydrolyzate to the required concentration.

The products obtained by the process according to the invention are particularly suitable for use in cosmetics and foods.

The following Examples are intended to illustrate the invention without limiting it in any way.

EXAMPLES

1. General

In Table 1, the Examples according to the invention are identified as E1 to E3 while the Comparison Examples are identified as C1 to C2.

2. Examples 2.1. Description of the process according to the invention 2.1.1. Example E1

(a) Enzymatic hydrolysis 300 g of chromium shavings were suspended in 900 g of water at 60° C. The pH value was then adjusted to 9.5–10.5 by addition of calcium hydroxide. 0.6 g of a commercial alkaline protease was then added and the mixture was kept for 1 hour at 55° to 60° C. During this hydrolysis, the pH value was kept at 9.5 to 10.5 by addition of calcium hydroxide.

(b) Deactivation of the enzyme/filtration

The mixture was then heated to 100° C. and kept at that temperature for 15 minutes in order to deactivate the enzyme. To separate chromium hydroxide and any undissolved calcium hydroxide, the mixture was filtered at 95° C.

(c) Chemical hydrolysis

The pH value was increased to 11.0 by addition of more calcium hydroxide, followed by heating for 30 minutes to 90° C. in order further to hydrolyze the relatively high molecular weight protein hydrolyzate fragments obtained in the first stage. Undissolved calcium hydroxide and precipitated chromium oxide were then separated off by filtration. The protein hydrolyzate thus obtained was then analyzed for its chromium content in this dilute solution by atomic absorption spectroscopy. The results obtained (in μg/ml) can be found in Table 1.

(d) Further working up

In the filtrate, dissolved calcium was precipitated as calcium oxalate and filtered off. The protein hydrolyzate solutions were then adjusted to concentrations of 40% by weight and 50% by weight by distilling off water.

2.1.2. Example E2

The procedure was as in Example E1 except that, in step (c), the pH value was adjusted to 11.5 by addition of calcium hydroxide.

2.1.3. Example E3

The procedure was as in Example E1 except that, in step (c), the pH value was adjusted to 12.5 by addition of calcium hydroxide.

2.2. Description of the comparison tests 2.2.1. Comparison Example C1

The procedure was as described in 2.1.1. except that step (c), i.e. the chemical hydrolysis, was left out.

2.2.2. Comparison Example C2

The procedure was as in Example E1 except that, in step (c), the pH value as adjusted to 10.5 by addition of calcium hydroxide.

3. Evaluation of the tests

The protein hydrolyzates obtained (E1 to E3 and C1 and C2) were analyzed for their chromium content and their storage behavior. The results obtained are set out in Table 1. The chromium contents are expressed in μg/ml ("ppm") and are based on the aqueous product mixture.

As can be seen from Table 1, the products obtained by the process according to the invention (E1 to E3) have distinctly lower chromium contents than the products of the pure enzymatic hydrolysis (C1). In addition, the products produced by the process according to the invention remained clear in storage.

The fact that the pH value prevailing during the chemical hydrolysis is critical is clearly apparent from Example C2 from which it can be seen that excessively low pH values cause a significantly higher chromium content.

TABLE 1

| Example | Chemical hydrolysis Yes/no | pH value | Duration | Chromium content[a] (µg/ml) | Appearance of concentrated product[b] Immediately | After 3 days |
|---|---|---|---|---|---|---|
| E1 | Yes | 11.0 | 30 mins. | <0.2 | Clear | Clear |
| E2 | Yes | 11.5 | 30 mins. | <0.1[c] | Clear | Clear |
| E3 | Yes | 12.5 | 30 mins. | <0.1[c] | Clear | Clear |
| C1 | No | — | — | 2.1 | Clear | Cloudy |
| C2 | Yes | 10.5 | 30 mins. | 0.8 | Clear | Clear |

[a]Based on the dilute aqueous product mixture; average value of three measurements
[b]The remarks in this column apply equally to protein hydrolyzate concentrates with active substance contents of 40% by weight and 50% by weight.
[c]In the analysis method selected (atomic absorption spectroscopy), the detection limit was 0.1 µg/ml, i.e. the figure "<0.1" means that the chromium content was below the detection limit.

What is claimed is:

1. A process for the production of a low-chromium protein hydrolyzate comprising the steps of: (1) partially hydrolyzing a chromium-containing nonpartially-denatured protein in an aqueous medium in the presence of an alkalino earth metal oxide or hydroxide and in the presence of a proteolytic enzyme to form a partial hydrolyzate; and (2) further hydrolyzing said hydrolyzate in the presence of an alkaline earth metal oxide or hydroxide at a pH value of from about 11 to about 13.

2. The process of claim 1 wherein said chromium-containing protein is a chrome leather waste from leather production.

3. The process of claim 1 further comprising the step of filtering said partial hydrolyzate at temperature of from about 80° to about 100° C. to remove chromium hydroxide before carrying out step (2).

4. The process of claim 3 wherein said temperature is from about 90° to about 95° C.

5. The process of claim 10 wherein step (2) is carried out at a temperature of from about of 80° to about 100° C.

6. The process of claim 5 wherein said temperature is from about 90° to about 95° C.

7. The process of claim 1 wherein step (2) is carried out over a period of from about 5 to about 60 minutes.

8. The process of claim 1 wherein said alkaline earth metal oxide is calcium oxide.

9. The process of claim 10 wherein said alkaline earth metal hydroxide is calcium hydroxide.

10. The process of claim 1 wherein said process is carried out in a tanning mixer.

11. The process of claim 1 wherein following step (1) and before step (2) the proteolytic enzyme is deactivated.

12. The process of claim 11 wherein the proteolytic enzyme is deactivated by the use of heat.

13. The process of claim 1 wherein step (1) is carried out at a pH of from about 9.5 to about 11.

14. The process of claim 13 wherein said pH is from about 10 to about 11.

15. A process for the production of a low-chromium protein hydrolyzate comprising the steps of
   A) partially hydrolyzing a chromium-containing nonpartially-denatured protein in an aqueous medium in the presence of an alkaline earth metal oxide or hydroxide and in the presence of a proteolytic enzyme at a pH in the range of from about 9.5 to about 11 to form a partial hydrolyzate;
   B) heating the partial hydrolyzate to deactivate the enzyme;
   C) filtering the partial hydrolyzate at a temperature of from about 80° to about 100° C. to remove insoluble chromium compounds; and
   D) further hydrolyzing the partial hydrolyzate in the presence of an alkaline earth metal oxide or hydroxide at a pH of from about 11 to about 13.

16. The process of claim 15 wherein step D) is carried out at a temperature of from about 80° to about 100° C. for a period of from about 5 to about 60 minutes.

17. The process of claim 16 wherein said temperature is from about 90° to about 95° C.

18. The process of claim 15 wherein step A) is carried out at a temperature of from about 60° to about 75° C.

* * * * *